(12) United States Patent
Falck, Jr. et al.

(10) Patent No.: US 7,473,231 B2
(45) Date of Patent: Jan. 6, 2009

(54) METHOD AND APPARATUS FOR EXAMINING AN EYE

(75) Inventors: Francis Y. Falck, Jr., Stonington, CT (US); Robert W. Falck, Pawcatuck, CT (US)

(73) Assignees: Francis Y. Falck, Mystic, CT (US); Robert T. Falck, Mystic, CT (US)

( * ) Notice: Subject to any disclaimer, the term of this patent is extended or adjusted under 35 U.S.C. 154(b) by 1291 days.

(21) Appl. No.: 10/178,987

(22) Filed: Jun. 25, 2002

(65) Prior Publication Data

US 2003/0236470 A1    Dec. 25, 2003

(51) Int. Cl.
*A61B 13/00* (2006.01)

(52) U.S. Cl. ..................................... 600/558

(58) Field of Classification Search ......... 600/398–406, 600/489, 558, 561, 504
See application file for complete search history.

(56) References Cited

U.S. PATENT DOCUMENTS

| | | | | |
|---|---|---|---|---|
| 3,452,589 A | * | 7/1969 | Hargens et al. | 600/398 |
| 3,572,100 A | * | 3/1971 | Grolman et al. | 600/401 |
| 3,585,849 A | * | 6/1971 | Grolman | 600/401 |
| 3,706,304 A | | 12/1972 | Sisler | |
| 3,952,585 A | * | 4/1976 | Perkins et al. | 600/405 |
| 4,172,447 A | * | 10/1979 | Bencze et al. | 600/401 |
| 4,209,021 A | * | 6/1980 | Warming | 600/398 |
| 4,281,662 A | | 8/1981 | Brent | |
| 4,948,062 A | * | 8/1990 | Mahar et al. | 242/538.2 |
| 4,987,899 A | | 1/1991 | Brown | |
| 5,070,875 A | | 12/1991 | Falck et al. | 128/645 |
| 5,140,990 A | * | 8/1992 | Jones et al. | 600/480 |
| 5,190,042 A | * | 3/1993 | Hock | 600/405 |
| 5,203,331 A | | 4/1993 | Draeger | |
| 5,363,155 A | | 11/1994 | Urinowski et al. | |
| 5,474,066 A | * | 12/1995 | Grolman | 600/398 |
| 5,830,139 A | * | 11/1998 | Abreu | 600/405 |
| 6,110,110 A | | 8/2000 | Dublin, Jr. et al. | |
| 6,120,460 A | | 9/2000 | Abreu | |
| 6,123,668 A | | 9/2000 | Abreu | |
| 6,179,779 B1 | | 1/2001 | Falck et al. | 600/398 |

OTHER PUBLICATIONS

"Calculation of the Pulsatile Ocular Blood Flow", C.E.T. Krakau, Investigative Ophthalmology & Visual Science, vol. 33, No. 9, Aug. 1992, pp. 2754-2756.

"Estimation of pulsatile ocular blood flow from intraocular pressure", D.M. Silver, R.A. Farrell, M.E. Langham, V O'Brien, and P. Schilder, ACTA Ophthalmologica 67 (1989) Supplementum 19, pp. 25-29.

Information from Auto Tonometer Corporation website, Mar. 8, 2002.

* cited by examiner

*Primary Examiner*—Max Hindenburg
*Assistant Examiner*—Rene Towa
(74) *Attorney, Agent, or Firm*—Brown & Michaels, PC (57) ABSTRACT

An applanation tonometer and its operation involve an actuator pressing a prism with a variable and determinable force against a cornea of an eye while a source directs light to reflect from an applanation surface of the prism to a detector producing a detected light signal received by a microprocessor. Such a tonometer produces a diastolic phase signal and a systolic phase signal representing the complete intra ocular pressure experience of the eye being examined. The signal information allows combined diastolic and systolic IOP to be determined in several corroborating ways and also yields measures of ocular blood flow and tonography.

25 Claims, 5 Drawing Sheets

METHOD AND APPARATUS FOR EXAMINING AN EYE

TECHNICAL FIELD

Eye examining instruments and methods.

BACKGROUND

Our previous U.S. Pat. No. 5,070,875, entitled "Applanation Tonometer Using Light Reflection To Determine Applanation Area Size", and U.S. Pat. No. 6,179,779, entitled "Replaceable Prism System For Applanation Tonometer" U.S. Pat. No. 6,474,647, entitled "Method of Operating Tonometer", and U.S. Pat. No. 6,736,778, entitled "Replaceable Prism For Applanation Tonometer" suggest tonometers, tonometer operating methods, and tonometer prisms for measuring intra ocular pressure (IOP) of an eye. Our type of applanation tonometer has an actuator that presses a prism with a variable and determinable force against a cornea of an eye being examined while a source directs light to reflect from an applanation surface of the prism to a detector producing a detected light signal received by a microprocessor.

Our experiments and experiences with working prototypes improving upon the disclosures of our issued patents and pending applications have led to several related discoveries. We have found that by changing and adding to the eye examining procedures that are possible with instruments such as ours we can obtain considerably more diagnostic information than has previously been clinically available. These discoveries involve not only eye examining methods but also structuring and programming a tonometer to perform such methods to obtain new measurements and new information of value to A clinician concerning the health and functioning of an eye being examined. Such improvements are the subject of this application.

SUMMARY

The tonometers that are commonly used clinically have operated only during a diastolic phase and have measured only a diastolic intra ocular pressure (IOP). In contrast to this, we have discovered that our instrument can produce a useable signal during a systolic pulse occurring in an eye being examined. Upon exploring this, we found that a systolic phase signal from our instrument can be used to determine an ocular pulse pressure or a systolic IOP. This constitutes valuable additional information not obtainable with previous clinical tonometers. It provides a measure not only of diastolic IOP, but also of systolic IOP, and enables an average, weighted average, or mean IOP determination that more accurately represents the true or complete IOP experienced by the eye being examined.

Other experiments with IOP signals attainable from our instrument have led to eye examining methods differing from our previous suggestions. We have found, for example, that IOP can be determined from a slope of a signal obtained as prism pressing force is changed during a time interval. This has eliminated any need to applanate an eye to a predetermined applanation area.

We have also found that a prism pressing force variation range for IOP examining purposes can begin with a preliminary value and change from that value through a predetermined signal change range, rather than proceeding from a reference applanation area to a measurement applanation area. This method eliminates variations in corneal thickness and curvature of different eyes, since these variations are automatically compensated for by the preliminary value from which the predetermined signal excursion range proceeds.

Experience with systolic pulse signals produced by our instrument has led to discovery of other measurements available from examining an eye. We found that we can determine ocular blood flow derived from the departure of the detected light signal from the diastolic IOP during the systolic pulses. Moreover, we have found that we can determine a tonography measure from the way the detected light signal changes from a systolic pulse back to the diastolic phase. We can also determine tonography by measuring a preceding IOP; then pressing the prism against the eye with a predetermined force sufficient to raise the IOP for a predetermined interval; followed closely by determining a subsequent IOP. From this we can derive the tonography measure from the differences between the preceding and the subsequent IOP determinations. An ocular blood flow measurement, and a tonographic measurement of the effectiveness of an eye's trabecular meshwork add significant and previously inaccessible diagnostic information of value to a clinician.

Finally, to ensure that the additional information produced by our eye examining method and instrument is readily available to clinicians, we have made our instrument fast acting, compact, convenient, and objective in its operation. Besides producing much new information, our instrument automatically rejects false readings, and automatically requires concentric contact with a cornea at a proper orientation to attain an accurate reading. The microprocessor in our instrument can preferably store, send, and receive information to perform all the required tasks and operations and to co-operate with computers and other information processing equipment.

DETAILED DESCRIPTION

Figure 1:
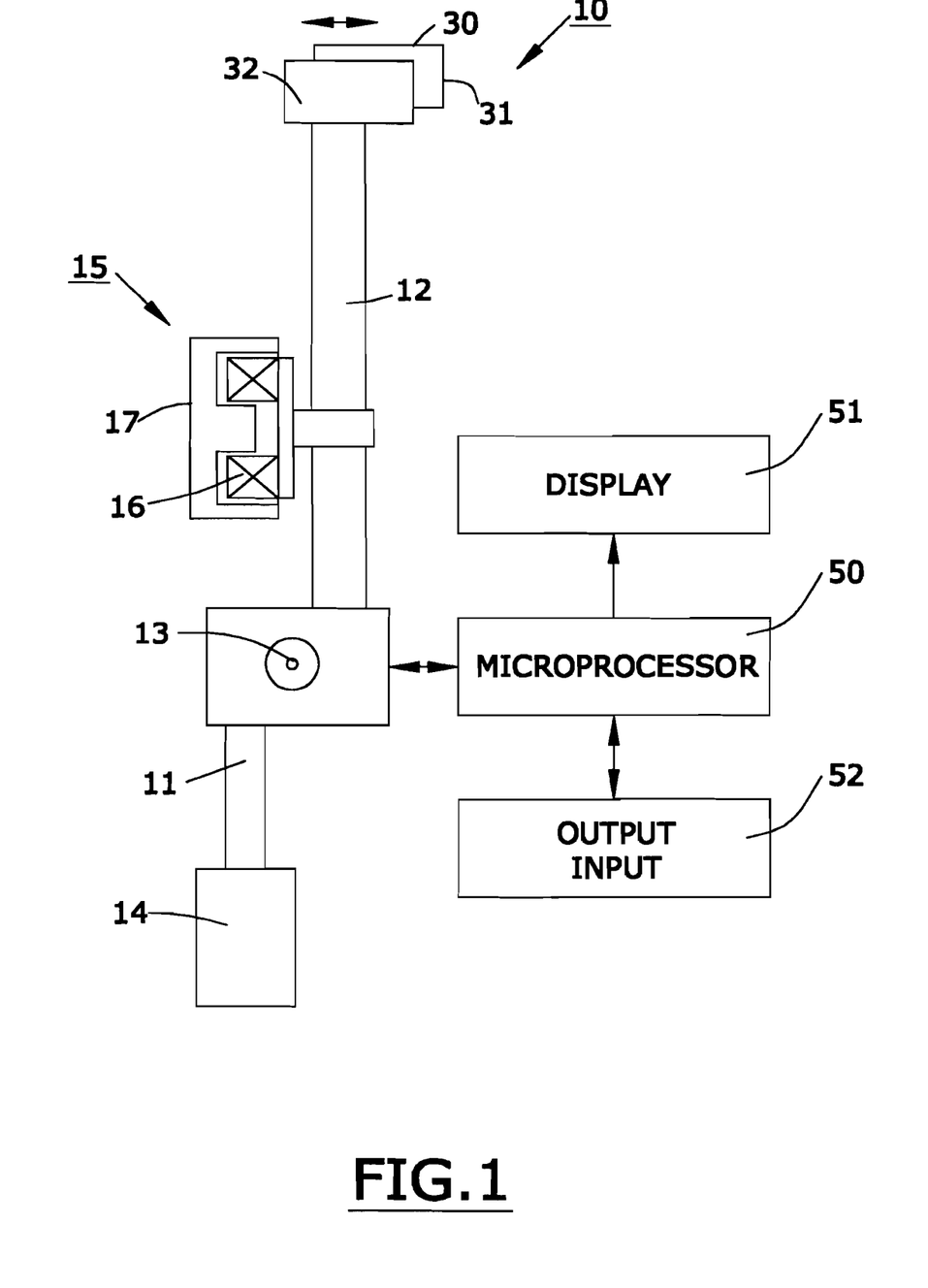
FIG. 1 is a schematic view of a preferred embodiment of our improved tonometer, which is suitable for practicing our inventive eye examinations.
Figure 2:
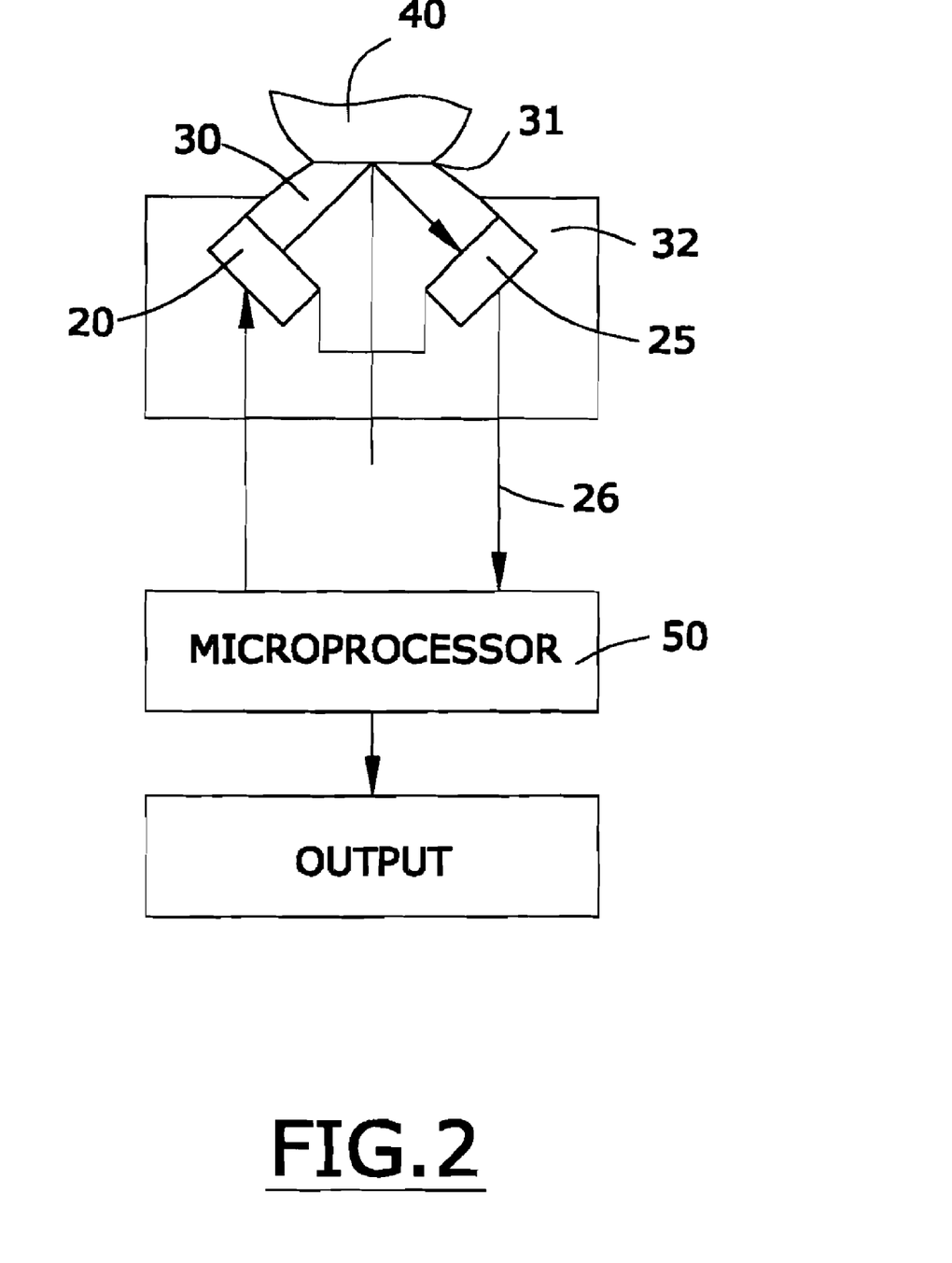
FIG. 2 is a schematic diagram of a portion of the tonometer of FIG. 1 involving a prism applanating an eye, a light source, a detector, a microprocessor, and an output.

Our eye examining method requires an instrument that can produce a signal representing intra ocular pressure (IOP) of an eye being examined. Such instruments are normally called tonometers, but our instrument and the ways it can be used produces information going beyond what can be expected of previous tonometers. Several variations of tonometers suitable for our purposes are described in our previous patents and applications. A presently preferred embodiment of such a tonometer 10 is schematically represented in FIGS. 1 and 2. Tonometer 10 preferably includes an actuator 15 pressing a prism 30 with a variable and determinable force against a cornea of an eye while a light source 20 directs light to reflect from an applanation surface 31 of prism 30 to a detector 25. In response to received light, detector 25 produces a detected light signal that is electrical in form and is sent to and analyzed by microprocessor 50 which in turn controls actuator 15 for varying the force of prism 30 pressing against the eye 40 and for varying the energization of light source 20. Microprocessor 50 also preferably drives a display 51 and preferably communicates with output and input devices 52.

The essential components of tonometer 10 include microprocessor 50, prism 30, some form of actuator 15, a light or radiation source 20, and a transducer or detector 25 receiving light or radiation reflected from applanation surface 31 and sending a corresponding electric signal to microprocessor 50. The precise working relationships among these essential components can be varied considerably, however, and the schematic illustrations of FIGS. 1 and 2 show only a presently preferred embodiment.

Prism 30 is preferably replaceable and disposable so that it can be removed from prism holder 32 after each examination and replaced with a fresh prism. This ensures that infectious agents, including the possibility of prions, are not transmitted from one pair of eyes to another.

Prism holder 32 is preferably mounted on arm 12, which is arranged to rotate or turn slightly around pivot 13. Since only a few millimeters of movement back and forth of prism 30 is required, as indicated by the double headed arrow, the rotational turning of arm 12 is slight.

A counter balance 14 arranged on arm 11 is arranged with a suitable moment arm relative to pivot 13 to return prism holder arm 12 to a base position. Proper arrangement and balancing of arms 11 and 12 around pivot 13 can eliminate the need for any return spring, and can enable instrument 10 to operate in different orientations.

Actuator 15 can be any of a variety of motors and other preferably electromagnetic prime movers. The preferred actuator schematically illustrated in FIG. 1 includes a coil 16 that is moveable relative to a permanent magnet 17, depending on the power supplied to coil 16. The relatively lighter coil 16 is preferably fixed to arm 12, and the relatively heavier permanent magnet 17 is preferably fixed to a body of instrument 10, because this reduces the rotating mass. It might also be possible to arrange permanent magnet 17 or coil 16 in the position of counter balance 14 to further reduce the rotational mass. Many other possibilities exist but for sake of conciseness and simplicity have not been illustrated.

Internal wiring within instrument 10 preferably connects a power supply (not shown) with microprocessor 50, which powers actuator 15, light source 20, and light detector 25. Microprocessor 50 preferably drives display 51 to display information directly to an instrument operator, and microprocessor 50 preferably has connections enabling it to receive and output information to and from other devices such as computer keyboards and number pads 52.

The light emitted by source 20 is preferably in a visible red region of the electromagnetic spectrum, but other colors of visible light are also possible, as is radiation energy at infra red or microwave frequencies. For simplicity, all of these possible different radiation frequencies are characterized as "light" within this application. As is well known, use of electromagnetic radiation at different frequencies can require angular adjustments so that light within prism 30 that is internally incident on applanation surface 31 is internally reflected to detector 25 except for a portion of the light that transmits into eye 40 through an applanation region of contact with prism surface 31. Of course, any radiation entering eye 40 must not cause injury.

Prism 30 is preferably molded of resin material to have a low enough manufacturing cost to be affordably disposable. Much more information on preferred characteristics of prism 30 is available in our U.S. Pat. No. 6,179,779 and our pending application Ser. No. 09/811,709. As we have previously suggested, microprocessor 50 is preferably programmed to require that prism 30 be replaced after being used for examining a pair of eyes. This is intended to prevent the tonometer prism from transporting infectious agents from the eyes of one person to the eyes of another.

Experiments and clinical experience with a working prototype of a tonometer instrument such as shown in FIGS. 1 and 2 has led to a simpler way of measuring a conventional diastolic intra ocular pressure (IOP). Our previous patents and applications recommended determining IOP from prism pressing force required to change between a reference applanation area (with a corresponding reference signal) and a measurement applanation area (with a corresponding measurement signal). We have now found that it is not necessary to use predetermined reference and measurement areas and corresponding signals to determine IOP.

Our new method preferably begins with a preliminary value of a detected light signal that the tonometer microprocessor is programmed to recognize. The preliminary value is preferably based upon preliminary contact of the prism applanation surface with a cornea at either bare contact pressure arising from surface tension of tears in the eye, or from a preferably very light predetermined prism pressing force.

The tonometer can be programmed to recognize that the preliminary value has occurred by noting the sudden reduction in the detected signal that occurs when the prism contacts the eye. Before this happens, all the light incident on prism applanation surface 31 is internally reflected, but when surface 31 contacts a cornea, a portion of the incident light is transmitted into the eye in the area of contact so that the detected light signal diminishes noticeably. The preliminary value signal can vary from eye to eye, as explained below, but can also serve as a starting point for an IOP determination.

Then instead of proceeding from the preliminary value to a measurement value, we proceed from the preliminary value through a range of values extending from the preliminary value. Any value at the end of the range extending from the preliminary value is not a fixed value, but is based only on distance from the preliminary value. To accomplish this, we program the microprocessor to operate actuator 15 to press prism applanation surface 31 against the cornea with increasing force applied during a time interval to change the detected light signal from the preliminary value through a range of values extending from the preliminary value. In doing this, microprocessor 50 preferably energizes actuator 15 to apply increasing prism force in predetermined increments that are applied in predetermined brief time intervals so that the detected light signal 26 varies in a step wise, sloped configuration as graphically illustrated in FIG. 3. Prism force changes and time intervals can also be continuous or analog, rather than being broken into the preferred increments. Also, prism force changes with respect to time are preferably linear, rather than non-linear, to simplify slope determinations.

Figure 3:
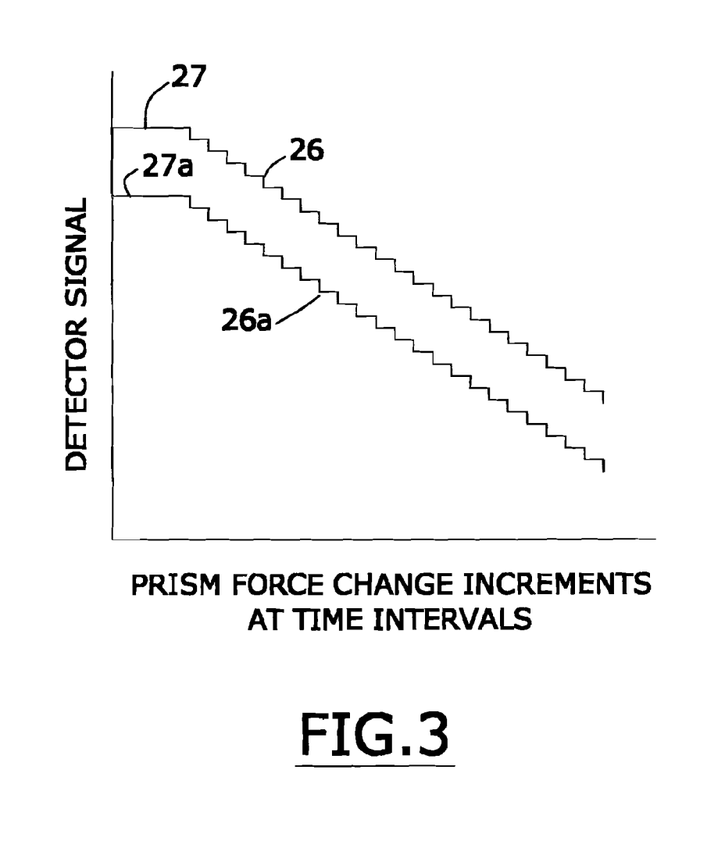
FIGS. 3-7 are schematic graphs of detector signals produced pursuant to our inventive eye examinations.

Signal 26 then provides several ways of determining IOP. One way is to proceed with increasing prism pressure force for a predetermined number of increments or for a predetermined time interval resulting in a predetermined increase in prism pressing force above the preliminary value. We then program microprocessor 50 to determine IOP from the signal change reached at the end value of the predetermined range of prism force change values. By a similar method, the force change values can be continued until the detected light signal 26 reaches a predetermined departure from the preliminary value, with microprocessor 50 determining IOP from the total pressure force required to reach the end signal value. Such an end signal value differs from the previously suggested measurement signal value by being related to the preliminary signal value 27 rather than being an absolute or independent value.

Another way that microprocessor 50 can determine IOP from detected light signal 26 is by measuring or detecting the slope as signal 26 changes over a time or force interval. We have found that signal slope alone is enough for microprocessor 50 to make an accurate determination of IOP. We have also found that detected signal slope tends to roll off at higher prism forces, so we prefer using a linear mid-region or lower force region of detected signal 26 for an IOP determination.

From an ophthalmologically known relation between IOP and force used in applanating a corneal area we have been able to apply linear, logarithmic, and logistic regression analyses to calculate IOP from the signals produced by instrument 10. In these analyses we have used the slope of the detected signal as changes in prism force change corneal applanation area and cause a corresponding change in signal value. Especially logistic regression analysis, which allows us to consider several variables at a time, has been useful in making force-to-signal-to-IOP calculations. We have also corroborated these results by Manometric comparisons and Goldmann tonometer readings.

Microprocessor 50 is preferably not programmed to make sophisticated mathematical calculations itself. We prefer instead that signal analysis be done separate from microprocessor 50, which is then programmed or loaded with a look up table from which it can determine IOP based on signal values. In doing this, microprocessor 50 can be programmed to average an IOP determination made by different methods.

These IOP determining methods can also be combined or used in conjunction so that one determination corroborates another. Moreover, elapsed time required to reach an end value can serve as another corroborator of an IOP determination. All the IOP determining methods can be combined in a single instrument that determines IOP according to each method and corroborates by comparing elapsed time, force change and electrical signal change. Any differences in the IOP determinations can be averaged out, unless differences are unusually large, in which case the microprocessor can be programmed to repeat the measurement. In a similar way, if elapsed time casts doubt on the accuracy of an IOP determination, the examination can be repeated.

These methods of IOP determination, besides being simple, accurate and fast, have another important advantage. By monitoring signal change relative to a predetermined value 27 that is not fixed but is related to each eye being examined, these IOP determining methods automatically take into account variations in corneal curvature and thickness. Our previous IOP determining suggestions envisioned separate measurements of corneal curvature and corneal thickness and input of such measurements to adjust IOP determinations. This is no longer necessary with our present IOP determining methods, because the preliminary signal value 27 is not a fixed value but is allowed to vary with each eye being examined.

This variation is schematically illustrated in FIG. 3 by the difference between preliminary value signals 27 and 27a, and the corresponding difference between detected signals 26 and 26a. More specifically, preliminary signal value 27 can be seen as a typical signal produced by contact of the tonometer prism with the cornea of a normal eye having a normally curved or arched cornea and a normal cornea thickness. Preliminary value signal 27a then indicates a preliminary contact signal from a cornea that is flatter or less arched than normal or a cornea that is thinner than normal. The value of preliminary signal 27a being less than the value of preliminary signal 27 indicates that preliminary prism contact with the thinner or flatter cornea has applanated a larger area. It would also be possible, but is omitted for the sake of simplicity, to show another preliminary value signal larger than signal 27, indicating preliminary contact with a cornea that is more arched than normal or is thicker than normal, resulting in applanation of a smaller area.

The ophthalmological literature indicates that every 50-micrometer variation in corneal thickness produces a 1.5 mm Hg variation in measured IOP. This variation will automatically appear in preliminary value signal 27 to adjust the starting point for a predetermined range of values. Similar indications are available in the ophthalmological literature for the effects of differences in arching or curvature of the cornea. These two translate into differences in measured IOP, which are automatically compensated for by preliminary signal value 27.

The variations in preliminary signal 27 due to corneal characteristics such as curvature and thickness do not matter in our present method of determining IOP, because change in detected light signal 26 or 26a, proceeds through a range extending from whatever preliminary value occurs. This automatically eliminates corneal curvature and thickness as possible variables in an IOP determination. The result is a more accurate IOP determination that does not have to be adjusted for corneal thickness or curvature and does not require any separate measurements of or adjustments for corneal thickness and curvature. This advantage can be especially important in examining eyes whose corneas have been modified for vision correcting purposes. The fact that such corneas can respond as thinner than normal does not prevent our tonometer from accurately measuring IOP.

We have also found that our tonometer instrument detects systolic pulses during eye examinations. Goldmann tonometers, which are ubiquitous in ophthalmological clinics, cannot make an IOP reading during a systolic pulse. Our instrument, in contrast, produces a detected light signal during both a diastolic phase and a systolic phase. This has led to several new ways of determining IOP, one of which is schematically graphed in FIG. 4.

Figure 4:
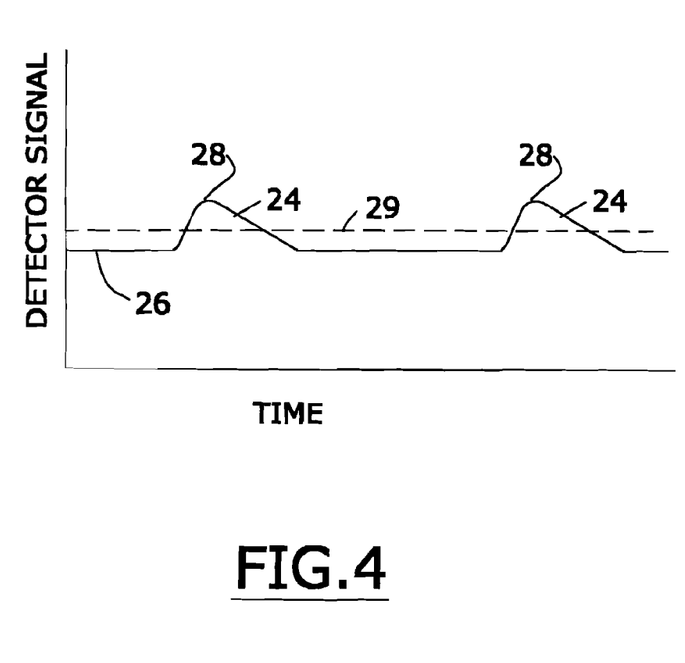

The process illustrated in FIG. 4 occurs after making a determination of diastolic IOP. For doing this, microprocessor 50 is preferably programmable to allow an operator to secure a reading only of diastolic IOP. Ocular pulse signals occurring during a systolic phase are then ignored by microprocessor 50 in making an IOP determination. Microprocessor 50 can also be programmed to proceed in several ways to determine a diastolic IOP while also taking into account the detected signal departure from a diastolic phase 26 during a systolic pulse.

For the method illustrated in FIG. 4, microprocessor 50 is programmed to operate actuator 15 to hold prism 30 against a cornea with a predetermined force for a long enough duration for two systolic pulses 28 to occur. These are illustrated in FIG. 4 as saw-tooth shaped increases in the otherwise flat diastolic signal 26. The height of systolic pulse signals 28 above diastolic signal 26 indicates ocular pulse pressure, and this is preferably used as an ingredient in an IOP determination. The fact that systolic pulse signals 28 are larger or higher than the diastolic phase signal 26 is because a systolic pulse slightly hardens the eye being examined, which reduces the area applanated by the tonometer prism 30 and increases the detected light signal.

The eye is subject not only to the IOP occurring in a diastolic phase, but also to the increased IOP that occurs during a systolic pulse when a bolus of blood flows into the eye. An IOP determination based only on a diastolic phase measurement therefore does not indicate the true pressure experienced by the eye over time. For example, a diastolic pressure might be 20 mm of mercury, while systolic pulse pressures reach 26 mm of mercury. A true IOP reading for all the pressure experienced by the eye over time should then include the systolic pulse pressures as a factor increasing the IOP over the diastolic phase pressure.

Broken line 29, as illustrated in FIG. 4, indicates an average, weighted average, or mean IOP determined not only from diastolic phase signal 26, but the increased height of ocular pulse signals 28, and a pulse rate. Microprocessor 50 is preferably capable of measuring time intervals and of calculating a pulse rate from the time elapsed between a pair of ocular pulse-pressure signals 28. Microprocessor 50 then preferably determines a mean or average IOP having a value higher than a diastolic phase measurement, based on the height and frequency of systolic pulse pressures. The systolic or ocular pulse pressure is calculated in a manner similar to the calculation of the diastolic IOP. The ocular pulse pressure can also be calculated as a percentage of the deviation from the diastolic phase IOP. Various regression analyses can be applied to these calculations, which can be corroborated manometrically.

Microprocessor 50 can also be programmed to determine only a systolic IOP, which can be done by ignoring diastolic signal phase 26. For most purposes, though, an average, weighted average, or mean IOP determination based on both diastolic and systolic phase signals is preferred.

The ability of our instrument 10 to produce usable systolic pulse signals 28 can also be used to determine ocular blood flow. This is preferably determined from the height of systolic pulse signals 28 above diastolic base line 26. The ophthalmological literature includes suggestions for calculating ocular blood flow from ocular pulse pressure by using a Friedenwald equation or one of the suggested modifications of the Friedenwald equation. Most of these suggestions focus on the height of signal 28 above a diastolic base line 26, as we prefer. Some suggestions have also focused on a leading edge of signal 28, and at least one proposal, which we have not adopted, suggests that the area under the signal 28 above the diastolic baseline 26 be considered. The various forms of regression analysis can also be applied to ocular blood flow calculations, and these can be corroborated by clinical experience. Whatever calculations are used, the results are preferably translated into a look up table programmed into microprocessor 50 for use in outputting ocular blood flow information.

Another measurement that becomes possible from the availability of ocular pulse-pressure signals 28 is a tonography measure of the effectiveness of the trabecular meshwork of the eye being examined. We prefer determining this from the downward or trailing slope 24 of the ocular pulse-pressure signal 28 as it returns from a peak pressure back to the diastolic base line 26. Generally, a steeper downward slope 24 indicates an effective trabecular meshwork that quickly returns from an elevated ocular pulse pressure back to a diastolic level. Conversely, a more gradual and extended downward slope 24 indicates a trabecular meshwork that is more impaired and recovers more slowly from a systolic pulse pressure.

Methods of calculating tonography measures from applanation signals are also available in the ophthalmological literature. These generally agree that down slope 24 is a key ingredient for tonography calculations. Like the IOP and ocular blood flow calculations, tonography measures can be refined by regression analyses and can be corroborated by clinical experience and by other measures; they are preferably translated into a look up table programmed into microprocessor 50.

The availability of a tonography measure, along with an ocular pulse pressure measure and an ocular blood flow determination gives a clinician considerably more information than has been available from tonometers. This additional information is valuable for both diagnostic and treatment purposes. Knowing the value of systolic pulse pressures and average or mean IOP gives information that is helpful in setting the aggressiveness of treatments used to reduce IOP. It can also help to determine whether to treat with drugs aimed at improving the effectiveness of the trabecular meshwork or whether to treat with drugs aimed at slowing down the production of ocular fluid. For example, using tonometer 10 to produce both an IOP determination and a tonography determination can affect a treatment method for an eye being examined. If the IOP determination is high enough to warrant treatment and the tonography determination is normal, then a clinician would treat the eye with a drug aimed at reducing production of aqueous fluid. On the other hand, if the IOP determination is high enough to warrant treatment and the tonography determination is subnormal, meaning that the trabecular meshwork of the eye is performing at a rate less than normal in removing aqueous fluid from the eye, then a clinician would treat the eye with a drug aimed at improving performance of the trabecular meshwork.

Knowing a measure of ocular blood flow can be relevant to these choices because some drugs can reduce ocular blood flow as a side effect. This must be guarded against so that ocular blood flow is not reduced enough to impair the health of the optic nerve and other eye components. Some drugs used in glaucoma treatment are either known or suspected of reducing ocular blood flow as a side affect, and having an ocular blood flow determination readily available can be used to avoid such drugs in a treatment aimed at reducing IOP.

Some drugs are also known to improve blood circulation generally, and these can be used if an ocular blood flow determination indicates that ocular blood flow of an eye being examined could advantageously be increased. This is the case with normal pressure glaucoma that impairs an optic nerve by reduction of ocular blood flow while an IOP determination remains normal. A clinician having tonometer 10 to make determinations of both IOP and ocular blood flow can diagnose that deterioration of an optic nerve is caused by subnormal ocular blood flow, without any increase in IOP. The appropriate treatment based on the low ocular blood flow determination provided by tonometer 10 would then be aimed at improving ocular blood flow, rather than reducing IOP. Drugs now exist that improve blood flow generally, and these can be tried and the results monitored by rechecking the eye for both IOP and ocular blood flow. Drugs may also be developed that will aim especially at increasing ocular blood flow while minimally affecting blood flow elsewhere.

Since ocular blood flow determinations have not previously been readily available to clinicians treating eyes for glaucoma, the effect of an ocular blood flow determination on eye treatment strategies has not been generally known. The ability of instrument 10 to provide such ocular blood flow information has many uses including monitoring an eye under treatment to be sure that the treated eye is not suffering from reduced ocular blood flow, which would call for a change in drugs being used in treatment. Having an ocular blood flow determination available from instrument 10 can also be beneficial in verifying that a drug aimed at increasing ocular blood flow in an eye experiencing normal pressure glaucoma has actually improved ocular blood flow. Knowing a tonography measure of the effectiveness of the eye's trabecular meshwork can also help monitor treatment determinations. For example, this can be used to determine the effectiveness of drugs intended to improve the working of the trabecular meshwork.

Figure 5:
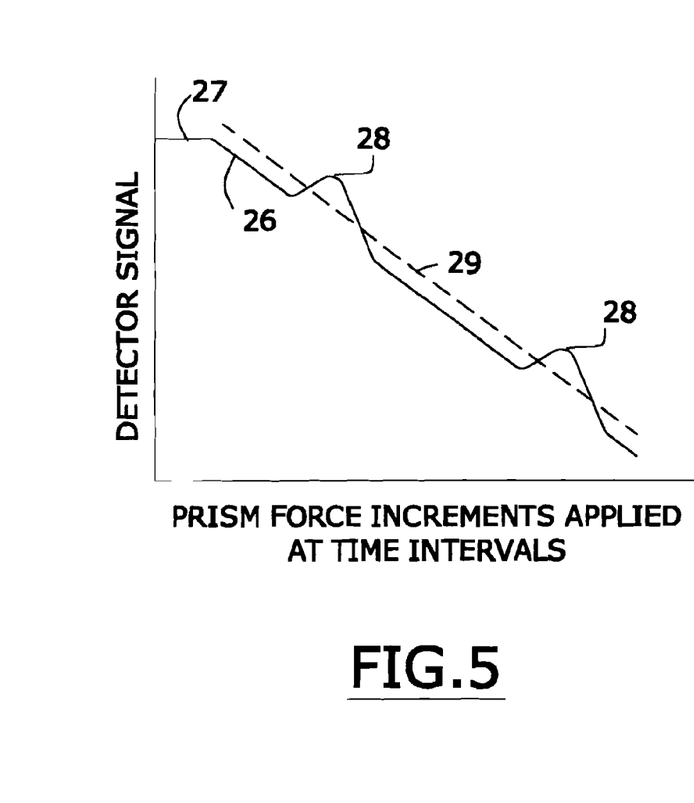

FIG. 5 illustrates the possibility of producing in a single examination excursion a signal that includes a preliminary value 27, a diastolic phase 26, and a systolic phase that includes ocular pulses 28. Such a signal would preferably extend for long enough to include two ocular pulses 28 so that microprocessor 50 can calculate a pulse rate. Of course, it is possible for such a signal to extend for a longer time, but this adds to the time that the prism is pressed against a patient's eye. A typical time needed to complete an examination excursion for diastolic purposes only is from 0.5 to 1.0 seconds. This would have to be extended somewhat to ensure that two systolic pulses 28 occurred for pulse rate determination.

The signals shown in FIG. 5 can be used to determine an average or mean IOP 29 as previously described, along with ocular pulse signals 28. Although diastolic baseline 26 is sloped because of the signal being generated while prism pressure increases over time, all the information necessary for determining IOP in the ways described above is available. An adjustment is needed for microprocessor 50 to take into account the sloping nature of the baseline signal 26 and the corresponding sloping nature of ocular pulse signals 28. Once the slopes are taken into account, all the necessary calculations for diastolic, systolic, and average or mean IOP can be calculated, along with ocular blood flow and a tonography measure.

Figure 6:
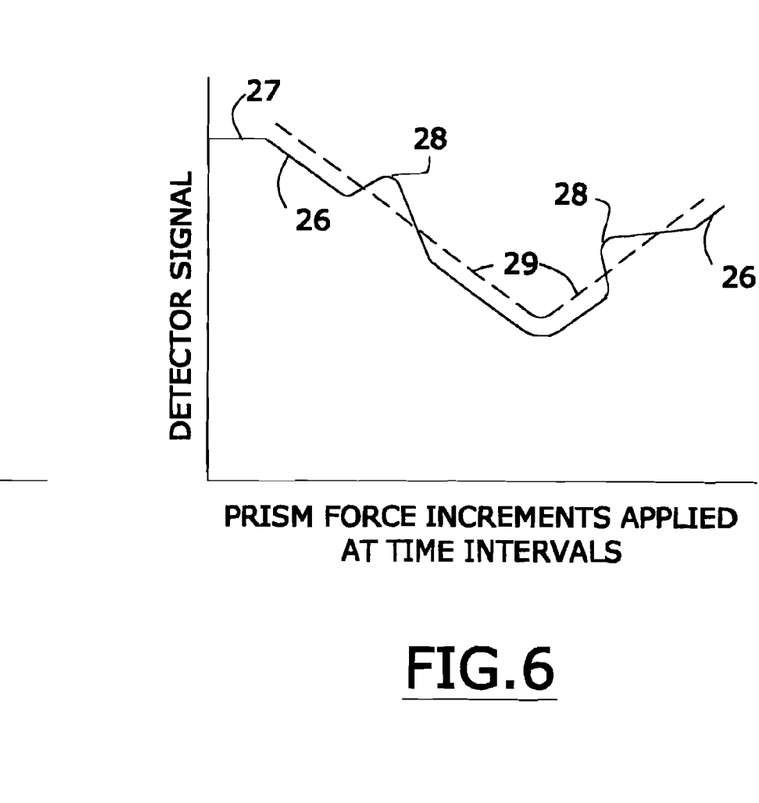

The embodiment of FIG. 6 illustrates the possibility of producing a signal during increasing prism pressure as signal 26 slopes downward, followed by diminishing prism pressure as signal 26 slopes back upward. Such a reversing signal can also extend for long enough to include at least two ocular pulses 28 from which pulse rate can be determined. Again, after taking into account the slopes caused by prism force changes over time, a signal such as illustrated in FIG. 6 can be used to make all the determinations described above.

Figure 7:
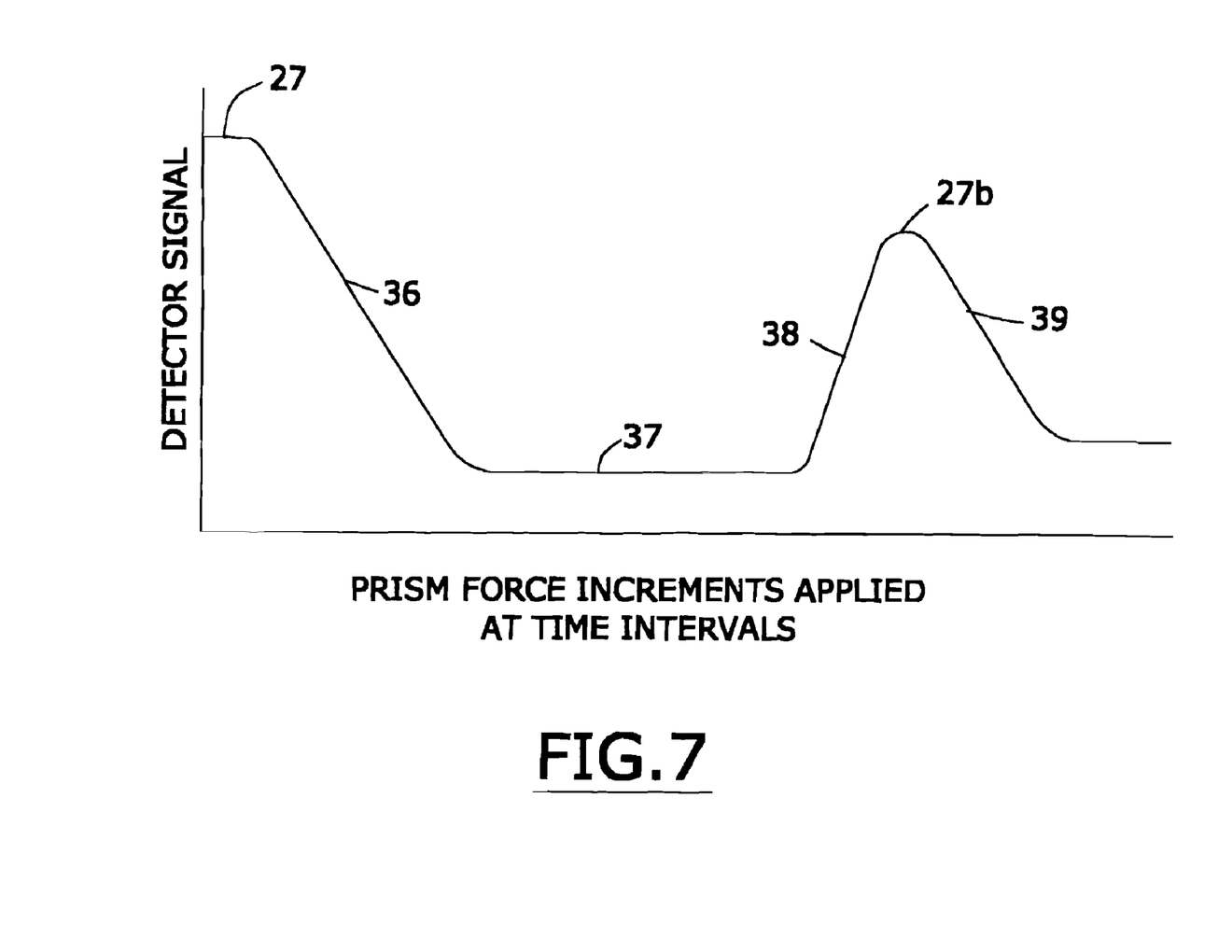

The embodiment of FIG. 7 schematically illustrates another way of determining a tonography measure by using tonometer 10. Beginning with preliminary signal value 27, microprocessor 50 is programmed to increase prism pressure force in one of the previously described ways to produce signal 36 (from which any systolic pulses have been eliminated) to make a preliminary determination of diastolic IOP. Prism force is then increased to produce signal 37, and prism force is sustained at that level for a predetermined interval. The prism force level for producing signal 37 is sufficient to raise the IOP of the eye to a level above the IOP determination made during the excursion-producing signal 36. During the interval that prism pressure force is elevated, as represented by signal 37, the eye that is subjected to the extra pressure attempts to accommodate to return its IOP to normal. The predetermined interval allowed for this is preferably in the range of a minute or two. Then prism pressure force is released, as represented by signal 38 and a new or subsequent IOP is determined as represented by signal 39 formed by increasing prism pressure from a preliminary value 27b.

The prism pressure force used to elevate the IOP to test the accommodating ability of the eye's trabecular meshwork is preferably sufficient to depress an ocular pulse signal during the predetermined interval that the prism force is applied. This results in the accommodation attempted by the trabecular meshwork to arise from the elevated IOP caused by the prism force as distinct from periodic accommodations following systolic pulses.

When elevated prism force is removed at the end of signal 37, the IOP of the previously pressurized eye reduces for a brief interval until the eye re-accommodates. During this interval a subsequent determination of diastolic IOP is made as represented by signal 39 showing that the IOP is reduced, and the eye has become temporarily softer. The difference between the higher IOP determined from signal 36 and the lower IOP determined from signal 39 gives a measure of the effectiveness of the trabecular meshwork of the eye. The healthier the eye, the greater will be the amount that the subsequent IOP is reduced from the preceding IOP.

This procedure is analogous to a known way of determining tonography by measuring IOP of an eye, and then while a patient is lying down, placing a weight on a patient's eye for an interval after which the IOP is again measured. Such a method is cumbersome and time consuming, since the patient has to lie down, and a weight has to be placed on the eye and then removed in between IOP determinations. By the method illustrated in FIG. 7, instrument 10 can make such a process much more efficient without requiring any weight and without requiring the patient to lie down.

We claim:

1. A method of measuring an ocular pulse pressure (OPP) of an eye, the method using a tonometer having an actuator pressing a prism with a variable force against a cornea of the eye while a source directs light to reflect from an applanation surface of the prism to a detector producing a detected light signal received by a programmed microprocessor and representing an applanated area of the cornea, the method comprising:

recognizing a preliminary value of the detected light signal occurring upon preliminary contact of the applanation surface with the cornea, the preliminary value varying from one eye to another based on specific corneal thickness and curvature of the eye being examined;

pressing the prism applanation surface against the cornea with increasing force applied during a time interval to change the detected light signal from the preliminary value through a range of values including the preliminary value extending by a predetermined amount from the preliminary value;

determining an intra ocular pressure (IOP) from changes in the detected light signal corresponding to prism pressure force changes in the range of values so that the IOP determination is substantially unaffected by thickness and curvature of the cornea of the eye being examined;

pressing the applanation surface against the cornea long enough for at least two systolic pulses to occur within the eye being examined; and determining OPP from departures of the detected light signal from the determined IOP during the systolic pulses.

2. The method of measuring OPP of claim 1 including determining a rate of the systolic pulses, and determining ocular blood flow from the pulse rate and the OPP.

3. A tonometer operated by the method of claim 1.

4. A method of measuring ocular pulse pressure (OPP) of an eye, the method using a tonometer that presses an applanation surface with a variable force against the cornea of an eye while a detector receives reflected light representing a varying size of an applanated area of the cornea and produces an applanated area signal delivered to a programmed microprocessor, the method comprising:

recognizing a preliminary value of the applanated area signal occurring upon preliminary contact of the applanation surface with the cornea, the preliminary value varying from one eye to another based on specific corneal thickness and curvature of the eye being examined;

pressing the applanation surface against the cornea with increasing force applied during a time interval to change the applanated area signal from its preliminary value through a range of values that include and extend from the preliminary value by a predetermined amount;

determining an intra ocular pressure (IOP) from changes in the applanated area signal corresponding to changes in the range of values so that the IOP determination is substantially unaffected by thickness and curvature of the eye being examined; and pressing the applanation surface against the cornea long enough for the microprocessor to detect from the applanated area signal at least two systolic pulses departing from the determined IOP; and determining the OPP from the departures of the applanated area signal occurring during the systolic pulses.

5. The method of measuring OPP of claim 4 including determining ocular blood flow based on the applanated area signal departures occurring during the systolic pulses and based on time intervals between the systolic pulses.

6. The method of measuring OPP of claim 4 including determining the IOP as a mean IOP, and determining the OPP based on the applanated area signal departures from the mean IOP during the systolic pulses.

7. The method of measuring OPP of claim 4 including determining a tonography measure based on a rate of change of the applanated area signal from a systolic pulse back to a diastolic state.

8. A tonometer operated by the method of claim 4.

9. A method of measuring intraocular pressure (IOP) of an eye, the method using a tonometer that presses an applanation surface with a variable force against the cornea of an eye while a detector receives reflected light representing a varying size of an applanated area of the cornea and produces an applanated area signal delivered to a programmed microprocessor, the method comprising:

recognizing a preliminary value of the applanated area signal occurring upon preliminary contact of the applanation surface with the cornea, the preliminary value varying from one eye to another based on specific corneal thickness and curvature of the eye being examined;

pressing the applanation surface against the cornea with increasing force during a time interval long enough for at least two systolic pulses to occur to change the applanated area signal from the preliminary value through a range of values that include and extend from the preliminary value by a predetermined amount while including values for the systolic pulses; and determining an IOP from changes in the applanated area signal corresponding to changes in the range of values so that the IOP determination includes a diastolic IOP value and a systolic IOP value and is substantially unaffected by thickness and curvature of the cornea of the eye being examined.

10. The method of measuring IOP of claim 9 including determining ocular pulse pressure (OPP) from departures of the applanated area signal from the determined IOP during the systolic pulses.

11. The method of measuring IOP of claim 10 including determining ocular blood flow from the OPP and a rate of the systolic pulses.

12. The method of measuring IOP of claim 9 including determining a tonography measure by using a change in the applanated area signal from a peak systolic pulse to a diastolic state.

13. A tonometer operated by the method of claim 9.

14. A tonometer operated by the method of claim 11.

15. A tonometer operated by the method of claim 12.

16. A method of measuring ocular blood flow (OBF) of an eye, the method using a tonometer that presses an applanation surface with a variable force against the cornea of an eye while a detector receives reflected light representing a varying size of an applanated area of the cornea and produces an applanated area signal delivered to a programmed microprocessor, the method comprising:

recognizing a preliminary value of the applanated area signal occurring upon preliminary contact of the applanation surface with the cornea, the preliminary value varying from one eye to another based on specific corneal thickness and curvature of the eye being examined;

pressing the applanation surface against the cornea with increasing force applied during a time interval to change the applanated area signal from the preliminary value through a range of values that include and extend from the preliminary value by a predetermined amount;

determining an intra ocular pressure (IOP) from changes in the applanated area signal corresponding to changes in the range of values so that the IOP determination is substantially unaffected by thickness and curvature of the cornea of the eye being examined;

holding the prism against the cornea for a long enough duration for the applanated area signal to indicate that at least two-systolic pulses have occurred; and determining OBF from a rate of the systolic pulses and from a systolic departure of the applanated area signal from a diastolic phase.

17. A tonometer operated by the method of claim 16.

18. A method of measuring the tonography of an eye, the method using a tonometer that presses an applanation surface with a variable force against the cornea of an eye while a detector receives reflected light representing a varying size of an applanated area of the cornea and produces an applanated area signal delivered to a programmed microprocessor, the method comprising:

recognizing a preliminary value of the applanated area signal occurring upon preliminary contact of the applanation surface with the cornea, the preliminary value varying from one eye to another based on specific corneal thickness and curvature of the eye being examined;

pressing the applanation surface against the cornea with increasing force applied during a time interval to change the applanated area signal from the preliminary value through a range of values that include and extend from the preliminary value by a predetermined amount;

selecting the time interval to include a peak value of a systolic pulse;

determining an intra ocular pressure (IOP) from changes in the applanated area signal corresponding to prism pressure force changes in the range of values so that the IOP determination is substantially unaffected by thickness and curvature of the cornea of the eye being examined; and determining a tonography measure based on a return of the applanated area signal from the peak value of the systolic pulse to a diastolic value occurring during absence of a systolic pulse.

19. The method of claim 18 including determining ocular blood flow (OBF) based on the peak value of the systolic pulse and systolic pulse rate.

20. A tonometer operated by the method of claim 18.

21. A tonometer that presses an applanation surface with a variable and determinable force against a cornea of an eye while a detector receives reflected light representing a varying size of an applanated area of the cornea and produces an applanated area signal delivered to a programmed microprocessor, the tonometer comprising:

the microprocessor being programmed to determine an intra ocular pressure (IOP) based on both the applanated area signal received during a diastolic phase and the applanated area signal received during a systolic phase;

the applanation surface being pressed against the cornea of the eye for a long enough duration for the applanated area signal to indicate that at least two systolic phases have occurred;

the microprocessor being programmed to recognize a preliminary value of the applanated area signal occurring upon preliminary contact of the applanation surface with the cornea, the preliminary value varying from one eye to another based on specific corneal thickness and curvature of the eye being examined;

the microprocessor being programmed to press the applanation surface against the cornea with increasing force applied during a time interval to change the applanated area signal from the preliminary value through a range of values that include and extend from the preliminary value by a predetermined amount; and the microprocessor being programmed to determine from the applanated area signal an average or mean IOP, and an ocular pulse pressure (OPP) occurring during a systolic phase, these determinations being substantially unaffected by thickness and curvature of the cornea of the eye being examined.

22. The tonometer of claim 21 wherein the microprocessor is programmed to determine ocular blood flow from departures of the applanated area signal from the average or mean IOP during the systolic phases.

23. The tonometer of claim 21 wherein the microprocessor is programmed to determine a tonography measure based on a return of the applanated area signal from a systolic value occurring during a systolic-phase to a diastolic value occurring during absence of a systolic phase.

24. A tonometer comprising:

an applanation surface arranged to be pressed against a cornea of an eye being examined, the applanation surface being supported on a rotationally moveable arm;

an electromagnetic actuator arranged for pressing the applanation surface against the cornea with a predetermined and variable force;

the electromagnetic actuator including a permanent magnet and a coil one of which is mounted on the arm supporting the applanation surface and the other of which is mounted in a fixed position;

a counterbalance applying a rotational moment arm to return the movable arm to a starting position without requiring a return spring;

a detector receiving reflected light indicating a varying size of an area of the cornea applanated by the applanation surface;

a microprocessor programmed to recognize a preliminary value of the applanated area signal occurring upon preliminary contact of the applanation surface with the cornea, the preliminary value varying from one eye to another based on specific corneal thickness and curvature of the eye being examined;

the microprocessor being programmed to press the applanation surface against the cornea with increasing force applied during a time interval to change the applanated area signal from the preliminary value through a range of values that include and extend from the preliminary value by a predetermined amount; and the microprocessor being programmed to determine an intra ocular pressure (IOP) from changes in the applanated area signal corresponding to changes in the range of values so that the IOP determination is substantially unaffected by thickness and curvature of the cornea of the eye being examined.

25. The tonometer of claim 24 wherein the applanation surface is replaceable, and the microprocessor is programmed to require replacement of the applanation surface after the applanation surface has been used for examining a pair of eyes of a patient.

* * * * *